United States Patent [19]

Banks

[11] Patent Number: 4,508,850

[45] Date of Patent: Apr. 2, 1985

[54] OLEFIN METATHESIS CATALYST

[76] Inventor: R. L. Banks, c/o Phillips Petroleum Company, Bartlesville, Okla. 74004

[21] Appl. No.: 579,334

[22] Filed: Feb. 13, 1984

Related U.S. Application Data

[62] Division of Ser. No. 506,950, Jun. 22, 1983, Pat. No. 4,454,368.

[51] Int. Cl.$^3$ .................. B01J 21/04; B01J 21/06; B01J 23/14
[52] U.S. Cl. .................. 502/351; 502/352; 502/355
[58] Field of Search ............ 502/351, 355, 300, 352

[56] References Cited

U.S. PATENT DOCUMENTS

| | | | |
|---|---|---|---|
| 3,642,931 | 2/1972 | Turner et al. | 260/683 D |
| 3,658,927 | 4/1972 | Crain et al. | 260/666 A |
| 3,676,520 | 7/1972 | Heckelsberg | 585/647 |
| 3,723,563 | 3/1973 | Bradshaw | 260/683 D |
| 4,215,017 | 7/1980 | Reusser | 502/355 X |

*Primary Examiner*—W. J. Shine

[57] ABSTRACT

Olefins are converted into other olefins having different numbers of carbon atoms by contact with a catalyst produced by contacting an inorganic refractory oxide support containing rhenium oxide with a promoting amount of at least one aluminum alkyl and, optionally, at least one tin alkyl compound under conditions suitable for aluminum and tin alkyl compounds to promote the activity of the rhenium oxide for the disproportionation reaction.

20 Claims, No Drawings

OLEFIN METATHESIS CATALYST

BACKGROUND OF INVENTION

This is a divisional application of my copending application having Ser. No. 506,950, filed June 22, 1983, entitled "Olefin Metathesis and Catalyst", now U.S. Pat. No. 4,454,368.

This invention relates to the disproportionation (metathesis) of olefins. In accordance with one aspect, this invention relates to a catalyst suitable for use in the disproportionation of acyclic olefinic hydrocarbons. In accordance with another aspect, this invention relates to a process for the disproportionation of acyclic olefinic hydrocarbons. In accordance with a further aspect, this invention relates to a catalyst suitable for use in the disproportionation of acyclic olefins comprising rhenium oxide, a support and at least one aluminum alkyl compound. In accordance with a further aspect, this invention relates to a catalyst suitable for use in the disproportionation of acyclic olefins comprising rhenium oxide promoted with at least one aluminum alkyl compound and at least one tin alkyl compound. In accordance with another aspect, this invention relates to a process for the disproportionation of acyclic olefinic hydrocarbons with a disproportionation catalyst as hereinbefore described under conditions of temperature and pressure which effect disproportionation of the feed.

The disproportionation, or metathesis, of olefins is a reaction in which one or more olefinic compounds are transformed into other olefins of different molecular weights. The disproportionation of an olefin with itself to produce an olefin of a higher molecular weight and an olefin of a lower molecular weight can also be referred to as a self-disproportionation. For example, propylene can be disproportionated to ethylene and bis-, and trans-2-butene. Another type of disproportionation involves the co-disproportionation of two different olefins to form still other olefins. An example would be the reaction of one molecule of 2-butene with one molecule of 3-hexene to produce two molecules of 2-pentene.

By the term "disproportionation" or "metathesis" throughout this specification is meant the conversion of the feed olefinic (or unsaturated) hydrocarbon to a mixture of olefinic (or unsaturated) hydrocarbons having lower and higher carbon numbers than the feed hydrocarbons.

Among the catalysts that have been developed for disproportionation are those comprising inorganic, refractory oxides containing a catalytic amount of rhenium oxide. The present invention is based upon the discovery of a way to improve the activity of such a catalyst.

Accordingly, an object of this invention is to provide a method for the conversion of olefins.

Another object of this invention is to provide a catalyst for the conversion of olefins.

Still another object of this invention is to provide a method for converting olefins to similar olefins of higher and lower numbers of carbon atoms.

Still another object is to provide a method for improving the activity of a rhenium catalyst for the conversion of olefins into similar olefins of higher and lower numbers of carbon atoms.

Other aspects, objects and the several advantages of the invention will be apparent to one skilled in the art upon reading the disclosure including a detailed description of the invention and the appended claims.

SUMMARY OF INVENTION

In accordance with the present invention, a disproportionation (metathesis) catalyst comprising an inorganic refractory oxide containing a catalytically effective amount of rhenium oxide is improved by contacting the catalyst with a promoting amount of at least one aluminum alkyl compound under conditions suitable for the aluminum alkyl to promote the activity of rhenium oxide.

Further, in accordance with the present invention, a disproportionation (metathesis) catalyst comprising an inorganic refractory oxide containing a catalytic amount of rhenium oxide is improved by contacting the rhenium oxide catalyst with a promoting amount of at least one aluminum alkyl compound and at least one tin alkyl compound under conditions suitable for the aluminum alkyl and tin alkyl compounds to promote the activity of rhenium oxide.

Also according to the invention, a process is provided for the disproportionation of an acyclic olefinic hydrocarbon by contacting the same with a disproportionation catalyst as hereinbefore described under conditions of temperature and pressure which effect disproportionation of the feed.

DESCRIPTION OF PREFERRED EMBODIMENTS

Inorganic refractory oxide supports that can be used include solid inorganic oxides comprising Group IVB metal oxides such as a titanium dioxide and zirconium dioxide. Titanium dioxide is presently preferred as the support.

Rhenium oxide can be combined with the support in any conventional manner such as dry mixing, impregnation from a diluent, ion exchange, or the like. The oxides can be added directly or in the form of rhenium compounds that can be converted to oxides by calcination. Calcination is conducted by heating the impregnated support in the presence of an oxygen-containing gas, such as air, under conditions sufficient to convert the rhenium compound to the oxide. Temperatures in the range of about 350° C. to about 800° C. are generally satisfactory for such calcination.

The proportion of the rhenium oxide (rhenium heptoxide) combined with the support can vary appreciably but generally the support will contain at least 0.1 percent by weight of rhenium oxide with amounts from 0.2 to about 40 percent by weight being preferred and about 2 to about 20 percent by weight especially preferred. The weight percent referred to is based on the combined weights of the support and the rhenium oxide.

The rhenium oxide catalyst is combined with a promoting amount of an aluminum alkyl compound of the formula $AlR_3$ wherein each R independently can range from 1 to about 6 carbon atoms. Representative examples of suitable aluminum alkyl compounds include trimethylaluminum, triethylaluminum, tributylaluminum, trihexylaluminum, and the like, as well as mixtures thereof.

The amount of promoting aluminum alkyl employed can vary depending upon the level of activation desired. Generally, the aluminum alkyl will be employed in an amount in the range of about 1 to about 100, preferably about 5–40 weight percent based on the total weight of the rhenium oxide catalyst prior to the addition of the aluminum alkyl.

The aluminum alkyl can be combined with the rhenium catalyst in any suitable manner. The aluminum alkyl is preferably contacted with the rhenium oxide catalyst in a hydrocarbon diluent and can be applied to the rhenium catalyst by spraying, immersing, or other liquid treatment.

It is essential that the combination of the aluminum alkyl and the rhenium catalyst be heated to an elevated temperature sufficient to cause the promotion to take place. Generally, this involves heating the catalyst to at least 200° C. The length of time of heating the catalyst composite is generally in the range of about 15 minutes to about 24 hours. It is accordingly currently preferred to apply the aluminum alkyl to a bed of the rhenium catalyst and then flow a suitable oxygen-containing gas, such as air, through the bed at a temperature in the range of about 350° C. to about 800° C. for a length of time sufficient to activate the catalyst. Typically, less time is required at higher temperatures and vice-versa. If desired, the thus calcined catalyst can be further treated with an inert gas such as nitrogen prior to use in the disproportionation reaction.

In accordance with a further embodiment of the invention, an aluminum alkyl promoted rhenium oxide catalyst after calcination can be additionally promoted by incorporation of a tin alkyl, such as tetramethyl tin. Suitable tin alkyl compounds of the formula $SnR_4$ that can be used include those with each R independently having from 1 to about 6 carbon atoms such as tetramethyl tin, tetraethyl tin, tetrabutyl tin, tetrahexyl tin, and the like, and mixtures thereof.

The amount of promoting tin alkyl employed can vary depending upon the level of activation desired. Generally, a tin alkyl will be employed in an amount of 0.5 to about 100, preferably 1–40, weight percent based on the total weight of rhenium oxide catalyst prior to the addition of the tin alkyl.

The tin alkyl can be combined with the rhenium oxide catalyst in any suitable manner. One preferred mode of combining tin alkyl with the rhenium catalyst is to contact the catalyst with a hydrocarbon solution of the tin alkyl. Following contact with a bed of the catalyst, for example in the reactor, the solvent can be removed by stripping with suitable gas flow or otherwise treating. The catalyst is then immediately suitable for use in the disproportionation reaction.

Olefins applicable for use in the process of the invention are non-tertiary, non-conjugated acyclic mono- and polyenes having at least 3 carbon atoms per molecule including cycloalkyl, cycloalkenyl, and aryl derivatives thereof; cyclic and polycyclic mono- and polyenes having at least 4 carbon atoms per molecule including alkyl and aryl derivatives thereof; mixtures of the above olefins; and mixtures of ethylene and the above olefins. Many useful reactions are accomplished with such acyclic olefins having 3–30 carbon atoms per molecule and with such cyclic olefins having 4–30 carbon atoms per molecule. Nontertiary olefins are those olefins wherein each carbon atom, which is attached to another carbon atom by means of a double bond, is also attached to at least one hydrogen atom.

Some specific examples of acyclic olefins suitable for reactions of this invention include propylene, 1-butene, 2-butene, 1-pentene, 2-pentene, 1-hexene, 1,4-hexadiene, 2-heptene, 1-octene, 2,5-octadiene, 2-nonene, 1-dodecene, 2-tetradecene, 1-hexadecene, 1-phenylbutene-2, 4-octene, 3-eicosene, 3-hexene, 1,4-pentadiene, 1,4,7-dodecatriene, 2-methyl-4-octene, 4-vinylcyclohexane, 1,7-octadiene, 1,5,9,13,17-octadecapentaene, 8-cyclopentyl-4,5-dimethyl-1-decene, 6,6-dimethyl-1,4-octadiene, and 3-heptene, and the like, and mixtures thereof.

Some specific examples of cyclic olefins suitable for the reactions of this invention are cyclobutene, cyclopentene, cycloheptene, cyclooctene, 5-n-propylcyclooctene, cyclodecene, cyclododecene, 3,3,5,5-tetramethylcyclononene, 3,4,5,6,7-pentaethylcyclodecene, 1,5-cyclooctadiene, 1,5,9-cyclododecatriene, 1,4,7,10-cyclododecatetraene, 6-methyl-6-ethylcyclooctadiene-1,5, and the like, and mixtures thereof.

The reaction temperature can vary depending upon the catalyst and feed(s) employed. Typically, the disproportionation is carried out at a temperature in the range of about 0° to about 300° C., preferably from about 20° to about 150° C.

The disproportionation reaction can be carried out by contacting the olefins to be disproportionated with the catalyst in the liquid phase or the gas phase depending on structure and molecular weight of the olefin. Pressure during the disproportionation reaction can vary between wide limits. For example, pressures between 0.1 and 500 atmospheres are suitable, although preferred pressures are between about 1 and 40 atmospheres.

If the reaction is carried out in the liquid phase, solvents or diluents for the reactants can be used. Aliphatic saturated hydrocarbons, e.g., pentane, hexanes and cyclohexane, dodecane and aromatic hydrocarbons such as benzene and toluene are suitable. If the reaction is carried out in the gaseous phase, diluents such as aliphatic hydrocarbons, for example, methane, ethane, and/or substantially inert gases, e.g., nitrogen, argon, can be present. Preferably, the disproportionation reaction is effected in the absence of significant amounts of deactivating materials, such as water and oxygen.

The contact time needed to obtain a reasonable yield of disproportionated products depends upon several factors such as the activity of the catalyst, temperature, pressure and structure of the olefinically unsaturated compound to be disproportionated. Length of time during which the olefinic unsaturated compounds to be disproportionated are contacted with the catalyst can conveniently vary between 0.1 second and 24 hours, although longer and shorter contact times can be used. Preferably, times of about 1 second to about 1 hour are used.

The process of the invention can be effected batchwise or continuously with fixed bed catalyst beds, slurried catalyst, fluidized beds, or by using any other conventional contacting techniques.

A further understanding of the present invention and its advantages will be provided by reference to the following examples.

All runs were made by passing a propylene feed through a stainless steel pipe vertical tubular reactor ($\frac{1}{2}$ inch diameter by 25 cm length) positioned in a temperature-controlled electric furnace. In each run the reactor contained a bed of the designated catalyst. A thermocouple was positioned in the catalyst bed to monitor reaction temperature.

The propylene feed was of a polymerization grade as sold by Phillips Petroleum Company of Bartlesville, Okla. The propylene feed was pretreated with activated Alcoa H151 alumina and activated magnesia prior to metathesis. The feed was passed downwardly through the vertically oriented tubular reactor.

Reaction product analysis was made by gas-liquid chromatography (glc) employing a Hewlett-Packard model 5880A chromatograph having a ⅛ inch by 20 ft. column packed with 19 percent bis-2-methoxyethoxyethylene (BMEE)+1 percent squalene on 60/80 Chrom P. Analysis was carried out isothermally at a temperature of about 30° to 40° C. with a helium carrier gas flow rate of about 20 mL/min.

EXAMPLE I

Five different catalyst compositions were prepared to be tested for propylene metathesis.

Control catalyst A was prepared by adding a solution containing 3.6 g ammonium perrhenate in 35 mL of water to 30 g of titanium dioxide powder. The resulting slurry was dried on a hot plate with constant stirring. A 5.0 g portion of −20+60 mesh catalyst was placed in the reactor and activated by heating at 550° C. for 60 minutes in flowing dry air, then for 30 minutes in dry nitrogen. The rhenium content of catalyst A was calculated to be 10.8 weight percent rhenium heptoxide. After cooling to 40° C., it was ready to metathesize propylene.

Control catalyst B was prepared starting with 5.0 g of catalyst A that had been activated as described above. After cooling under nitrogen to room temperature the catalyst was transferred, under nitrogen, to a flask. After evacuation of the flask the catalyst was sprayed with 5 mL of a solution of 25 percent tetramethyltin in cyclohexane. Solvent was removed by evacuation and the catalyst, under a nitrogen atmosphere, was transferred to the reactor. After warming to 40° C., the catalyst which contained 20 weight percent tetramethyltin on catalyst A was ready to metathesize propylene.

Preparation of control catalyst C was identical to that of catalyst B except that the activated and cooled catalyst was sprayed with 5.8 mL of a solution of 25 percent triethylaluminum in n-hexane. After removal of solvent by evacuation, catalyst C was calculated to contain 20 weight percent triethylaluminum on catalyst A.

Invention catalyst D was obtained by activating the composition of catalyst C in the reactor at 550° C. for 60 minutes in flowing dry air, then for 30 minutes in dry nitrogen.

Invention catalyst E was prepared by addition of tetramethyltin to catalyst D. The procedure used was identical to that described for the preparation of catalyst B. After removal of solvent by evacuation, catalyst E was placed in the reactor, warmed to 40° C., and ready to metathesize propylene.

EXAMPLE II

The catalysts prepared as described above were tested for propylene metathesis activity at a temperature of 40° C., pressure of 75 psig and a propylene feed rate of 4 weight hourly space velocity (WHSV). In all runs, 5.0 grams of catalyst were employed. Conversion of propylene feed to ethylene plus butenes was determined by glc, and is summarized in the Table.

TABLE

| Catalyst | Propylene Conversion, % Time, minutes | | | |
|---|---|---|---|---|
| | 5 | 30 | 60 | 120 |
| A | 5.6 | 0.3 | — | — |
| B | tr. | tr. | — | — |

TABLE-continued

| Catalyst | Propylene Conversion, % Time, minutes | | | |
|---|---|---|---|---|
| | 5 | 30 | 60 | 120 |
| C | 0.8 | 0.3 | 0.3 | — |
| D (Invention) | 22.4 | 15.9 | 12.6 | — |
| E (Invention) | 35.3 | 35.8 | 35.8 | 33.7 |

The results of these experiments demonstrate the increased catalyst activity achieved upon catalyst treatment with triethylaluminum followed by activation in dry air at 550° C. Additional catalyst activation is observed upon further treatment of the inventive catalyst with tetramethyltin, while direct treatment of $Re_2O_7$—$TiO_2$ catalyst with tetramethyltin (catalyst B) appeared to be detrimental to catalyst metathesis activity.

That which is claimed is:

1. A composition suitable for the disproportionation of olefins comprising the product produced by contacting rhenium oxide and a support with a promoting amount of at least one aluminum alkyl compound and heating the aluminum alkyl treated rhenium oxide to a temperature of at least about 200° C. suitable for said aluminum alkyl to promote the activity of said rhenium oxide for the disproportionation reaction.

2. A composition according to claim 1 wherein said aluminum alkyl is a compound of the formula $AlR_3$ wherein each R independently can range from 1 to about 6 carbon atoms and the amount of aluminum alkyl employed ranges from about 1 to about 100 weight percent of the combined weight of rhenium oxide and support prior to addition of aluminum alkyl.

3. A composition according to claim 1 wherein the rhenium oxide is combined with titanium dioxide support in an amount equal to about 1 to about 15 weight percent of the combined weights of rhenium oxide and titanium dioxide.

4. A composition according to claim 1 wherein said promoted rhenium oxide is calcined by heating to a temperature ranging from about 350° C. to about 800° C. for a length of time sufficient to activate the catalyst.

5. A composition according to claim 1 in which the calcined catalyst additionally contains a promoting amount of at least one tin alkyl compound.

6. A composition according to claim 5 wherein the amount of tin alkyl employed ranges from about 0.5 to about 100 weight percent of the combined weights of rhenium oxide and support.

7. A composition according to claim 5 wherein said tin alkyl is tetramethyl tin.

8. A composition according to claim 5 wherein rhenium oxide is combined with titanium dioxide support in an amount equal to about 1 to about 15 weight percent of the combined weights of rhenium oxide and titanium dioxide and the amount of aluminum alkyl employed is in the range of about 5 to about 40 weight percent and the amount of tin alkyl employed ranges from about 1 to about 40 weight percent of the combined weights of rhenium oxide and titanium dioxide prior to the addition of aluminum and tin alkyl.

9. A composition according to claim 4 wherein said aluminum alkyl is triethylaluminum.

10. A composition suitable for the disproportionation of olefins comprising the product produced by contacting rhenium oxide on a support with a promoting amount ranging from about 1 to about 100 weight percent of the combined weights of rhenium oxide and support of at least one aluminum alkyl compound of the formula $AlR_3$ wherein each R independently can range from 1 to about 6 carbon atoms, and subjecting the promoted rhenium oxide to calcination conditions by heating to a temperature of at least about 200° C. suitable for said aluminum alkyl to promote the activity of said rhenium oxide for the disproportionation reaction.

11. A composition according to claim 10 wherein said aluminum alkyl is triethylaluminum.

12. A composition according to claim 11 wherein the rhenium oxide is combined with titanium dioxide support in an amount equal to about 1 to about 15 weight percent of the combined weights of rhenium oxide and titanium dioxide.

13. A composition according to claim 10 in which the calcined catalyst additionally contains a promoting amount of at least one tin alkyl compound of the formula $SnR_4$ wherein each R independently can have from 1 to about 6 carbon atoms.

14. A composition according to claim 13 wherein the amount of tin alkyl employed ranges from about 0.5 to about 100 weight percent of the combined weights of rhenium oxide and support.

15. A composition according to claim 14 wherein said tin alkyl is tetramethyl tin.

16. A composition according to claim 13 wherein rhenium oxide is combined with titanium dioxide support in an amount equal to about 1 to about 15 weight percent of the combined weights of rhenium oxide and titanium dioxide and the amount of aluminum alkyl employed is in the range of about 5 to about 40 weight percent and the amount of tin alkyl employed ranges from about 1 to about 40 weight percent of the combined weights of rhenium oxide and titanium dioxide prior to the addition of aluminum and tin alkyl.

17. A process for preparing a catalyst effective for the disproportionation of olefins which comprises incorporating into a supported rhenium oxide catalyst a catalytic promoting amount of at least one aluminum alkyl compound and subjecting the aluminum alkyl promoted catalyst to thermal treatment at a temperature of at least about 200° C. in the presence of an oxygen-containing gas.

18. A process according to claim 17 wherein a catalytic promoting amount of at least one tin alkyl compound is incorporated into said supported rhenium oxide catalyst after said thermal treatment.

19. A process according to claim 17 wherein said aluminum alkyl promoted catalyst is subjected to thermal treatment at a temperature ranging from about 350° to about 800° C.

20. A process according to claim 19 wherein a hydrocarbon solution of a tin alkyl compound is combined with the thermally treated catalyst and then heated sufficiently to remove solvent and leave a tin alkyl promoted catalyst suitable for use in a disproportionation reaction.

* * * * *

UNITED STATES PATENT AND TRADEMARK OFFICE
CERTIFICATE OF CORRECTION

PATENT NO. : 4,508,850

DATED : April 2, 1985

INVENTOR(S) : Robert L. Banks

It is certified that error appears in the above-identified patent and that said Letters Patent is hereby corrected as shown below:

On the title page;
Assignee on face of patent should be PHILLIPS PETROLEUM CO.

Signed and Sealed this

Thirteenth Day of August 1985

[SEAL]

Attest:

DONALD J. QUIGG

Attesting Officer

Acting Commissioner of Patents and Trademarks